(12) United States Patent
Abdolahad et al.

(10) Patent No.: US 10,556,234 B2
(45) Date of Patent: Feb. 11, 2020

(54) ISOLATION AND DETECTION OF CIRCULATING TUMOR CELLS (CTCS)

(71) Applicants: Mohammad Abdolahad, Tehran (IR); Seiedali Hosseini, Ghazvin (IR); Somayeh Zanganeh, Malayer (IR)

(72) Inventors: Mohammad Abdolahad, Tehran (IR); Seiedali Hosseini, Ghazvin (IR); Somayeh Zanganeh, Malayer (IR)

( * ) Notice: Subject to any disclaimer, the term of this patent is extended or adjusted under 35 U.S.C. 154(b) by 239 days.

(21) Appl. No.: 15/238,505

(22) Filed: Aug. 16, 2016

(65) Prior Publication Data

US 2017/0128939 A1 May 11, 2017

Related U.S. Application Data

(60) Provisional application No. 62/237,580, filed on Oct. 6, 2015.

(51) Int. Cl.
| | |
|---|---|
| *B01L 3/00* | (2006.01) |
| *C12Q 1/04* | (2006.01) |
| *G01N 15/10* | (2006.01) |
| *G01N 27/02* | (2006.01) |
| *G01N 33/50* | (2006.01) |

(52) U.S. Cl.
CPC ... *B01L 3/502753* (2013.01); *B01L 3/502715* (2013.01); *C12Q 1/04* (2013.01); *G01N 15/1031* (2013.01); *G01N 27/02* (2013.01); *G01N 33/5091* (2013.01); *B01L 2200/10* (2013.01); *B01L 2300/027* (2013.01); *B01L 2300/0645* (2013.01); *B01L 2400/0487* (2013.01); *G01N 2015/1006* (2013.01)

(58) Field of Classification Search
CPC ......... B01L 3/502753; B01L 3/502715; B01L 2200/10; B01L 2300/027; B01L 2400/0487; B01L 2300/0645; C12N 5/0695; C12N 2531/00; C12Q 1/04; G01N 15/1031; G01N 27/02; G01N 33/5091; G01N 2015/1006
See application file for complete search history.

(56) References Cited

U.S. PATENT DOCUMENTS

| | | | |
|---|---|---|---|
| 7,425,253 B2 * | 9/2008 | Voldman | B03C 5/005 204/547 |
| 2012/0100521 A1 | 4/2012 | Soper | |
| 2014/0248621 A1 * | 9/2014 | Collins | G01N 15/1031 435/6.12 |

OTHER PUBLICATIONS

Abdolahad (Biosensors and Bioelectronic 59 (2014) 151-159 (Year: 2014).*
Mohamed et al. (IEEE Transactions on nanobioscience, vol. 3, No. 4, Dec. 2004). (Year: 2004).*
Han et al. (Clin Cancer Res 2007; 13 (1) Jan. 1, 2007). (Year: 2007).*

(Continued)

*Primary Examiner* — Sally A Merkling
(74) *Attorney, Agent, or Firm* — Bajwa IP Law Firm; Haris Zaheer Bajwa

(57) ABSTRACT

An integrated system to isolate and diagnose circulating tumor cells (CTCs) within a cellular sample includes an isolating mechanism to isolate and trap large biological cells at a detection zone from among the cellular sample based on cells size, and includes a diagnosing mechanism to diagnose CTCs among the trapped large biological cells, based on cells electrical impedance.

18 Claims, 18 Drawing Sheets
(3 of 18 Drawing Sheet(s) Filed in Color)

(56) References Cited

OTHER PUBLICATIONS

Shannon L. Stott, Isolation of circulating tumor cells using a microvortex-generating herringbone-chip, Proceedings of the National Academy of Sciences, Aug. 24, 2010, vol. 107, Issue 43, pp. 18392-18397.

Waseem Asghar, Electrical fingerprinting, 3D profiling and detection of tumor cells with solid-state micropores, Lab on a Chip, May 1, 2012, vol. 12, Issue 13, pp. 2345-2352.

Arum Han, Quantification of the Heterogeneity in Breast Cancer Cell Lines Using Whole-Cell Impedance Spectroscopy, Clinical Cancer Research, Sep. 21, 2006, vol. 13, Issue 1, pp. 139-143.

H. Edward Ayliffe, Electric Impedance Spectroscopy Using Microchannels with Integrated Metal Electrodes, IEEE Journal of Microelectromechanical Systems, Mar. 1994, vol. 8, No. 1, pp. 50-57.

Igor Cima, Label-free isolation of circulating tumor cells in microfluidic devices: Current research and perspectives, Jan. 24, 2013, Biomicrofluidics, vol. 7, Issue 1, 011810.

Ling Yu, Advances of lab-on-a-chip in isolation, detection and post-processing of circulating tumour cells, Lab on a Chip, Apr. 22, 2013, vol. 13, Issue 16, pp. 3163-3182.

\* cited by examiner

ISOLATION AND DETECTION OF CIRCULATING TUMOR CELLS (CTCS)

CROSS REFERENCE TO RELATED APPLICATION

The present application claims priority from U.S. Provisional Patent Application Ser. No. 62/237,580, filed Oct. 6, 2015, entitled "Nanoelectromechanical chip (NELMEC)", which is incorporated by reference herein in its entirety.

TECHNICAL FIELD

The present application generally relates to an integrated system configured to screening, capturing, and detecting circulating tumor cells (CTCs) within a blood sample, and a method for use thereof.

BACKGROUND

Tumor Metastasis is a series of several sequential steps started by invasion of individual cells, which are named circulating tumor cells (CTCs), into the bloodstream. CTCs are originated from the primary tumor, and their enumeration procedures are known to be reliable methods in cancer staging and therapy monitoring, such as minimal residual disease (MRD). The number of CTCs has a good correlation with various clinical time points, such as overall survival (OS) and progression free survival (PFS).

Less than 5 CTCs is found per 1 ml of a blood sample taken from a cancer patient with a high survival rate. There are practical difficulties in detecting such rare cells among billions of red blood cells (RBCs) and millions of white blood cells (WBCs). Therefore, CTC detection often requires complicated blood enrichment steps.

Therefore, there is a need for an integrated system or method capable for both isolating and detecting the CTCs in a blood sample to diagnose the cancerous state or metastatic state at early stages of cancer progression.

SUMMARY

In one general aspect of the present disclosure, an integrated system for isolating and diagnosing circulating tumor cells (CTCs) within a cellular sample is disclosed. The system can include: an isolating mechanism for isolating (i.e., trapping) large biological cells at a detection zone from the cellular sample, based on cell sizes; and a diagnosing mechanism for diagnosing (or detecting) CTCs among the trapped biological cells using a diagnosing system, based on cells electrical impedance. Furthermore, the system can include a flow inlet configured for introducing an inlet flow that includes the cellular sample and a flow outlet configured for collecting an outlet flow of the remainder of the cellular sample.

The above general aspect may include one or more of the following features. The cellular sample may include a blood sample. The large biological cells may be biological cells having a cell size in a range of about 12 $\mu m$ to about 40 $\mu m$, including large WBCs or CTCs. In some cases, CTCs can include epithelial circulating tumor cells (ECTCs) or mesenchymal circulating tumor cells (MCTCs), or both.

In some implementations, the flow inlet can be configured to include a syringe pump and the flow outlet can be configured to include a collector dish.

The isolating mechanism can include an array of parallel microchannels vertically etched onto a microfluidic chip. Each microchannel can have a depth and a width with one inlet and one outlet for fluid flow. The width of the microchannels can be about 12 $\mu m$ and the depth of the microchannels can be about 15 $\mu m$. The detection zone can be a zone at the inlet of the microchannels, where the large biological cells are trapped.

The diagnosing system can include: (i) an array of electrical sensors, including one electrode, an electrical conductive path, and a readout pad; (ii) a signal controlling system that is configured for applying an electrical signal to the trapped biological cells attached to the electrical sensors and to acquire an electrical response corresponding to the electrical signal; and (iii) a data processor configured for analyzing the electrical response in order to diagnose the CTCs among the isolated large biological cells.

In some implementations, the electrodes can be positioned within the detection zone on the microfluidic chip, so that the isolated large biological cells can be attached to the electrodes. The electrodes can include a plurality of silicone nano-grass (SiNG) electrodes. Furthermore, the readout pads and the electrical conductive path can be made of gold.

In some implementations, the signal controlling system can include: an AC signal source configured for applying the electrical signal to the electrical sensors; a data acquisition module configured for acquiring the electrical response corresponding to the electrical signal from the electrical sensors; and a multiplexer module configured for selecting and controlling the electrical sensors for applying the electrical signal or acquiring the electrical response. In some implementations, the AC signal source may apply a voltage of about 40 mV to the electrical sensors. Correspondingly, the applied voltage may have a frequency in a range of about 100 Hz to 100 KHz.

In another aspect of the present disclosure, a microfluidic chip for isolating and diagnosing CTCs within a cellular sample is disclosed. The microfluidic chip can include: a chip having one input part and one output part for fluid flow that is positioned onto the chip; an array of parallel microchannels, each having one inlet and one outlet for fluid flow, which can be vertically etched onto the output part of the chip; and an array of electrical sensors, where each electrical sensor can include one electrode that is connected to a readout pad via an electrical conductive path on the chip. Each electrode can be positioned within the input part at the inlet of each microchannel. Furthermore, the microfluidic chip can include a cylindrical shaped inlet that is vertically positioned in the input part of the chip and a cylindrical shaped outlet that is vertically positioned in the output part of the chip.

In some implementations, the chip can include a silicon chip or wafer. A surface of the chip may be capped by a layer for electrical insulation. One example of such a layer is a polydimethylsiloxane (PDMS) layer. The electrodes can include a plurality of SiNG arrays, which may be fabricated via a reactive ion etching (RIE) method at the inlet of the microchannels.

In another aspect of the present disclosure, a method for isolating and diagnosing CTCs is disclosed. The method can include the steps of: isolating the CTCs along with other large biological cells from a cellular sample based on a size difference between large biological cells and other biological cells within the cellular sample; and detecting the CTCs presence among the isolated large biological cells and detecting their amount in the cellular sample based on an electrical impedance difference between CTCs and other large biological cells. The cellular sample can be a blood sample.

In one implementation, the isolating of CTCs can include introducing the cellular sample into the microfluidic chip of the present disclosure to traverse from the inlet to the outlet, so that the CTCs are trapped at the inlet of the microchannels and are attached to the electrodes. In some implementations, the cellular sample can be introduced into the microfluidic chip with a flow rate in a range of about 20 µL/min to about 160 µL/min.

In another implementation, the detection of CTCs can include: applying an electrical signal to an electrode using the signal controlling system of the present disclosure; measuring the electrical response of the electrode using the signal controlling system; and recording and processing the electrical response from the electrodes via the data processor of the present disclosure. The electrical response can be a criterion of those cells electrical impedance. The detection of CTCs can be done at the beginning of introduction of cellular sample into the microfluidic chip, in the middle of introduction (i.e., half or approximately half of the solution has reached to the outlet of the microfluidic chip) or at the end of introduction (i.e., the entire solution has left the outlet of the microfluidic chip).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
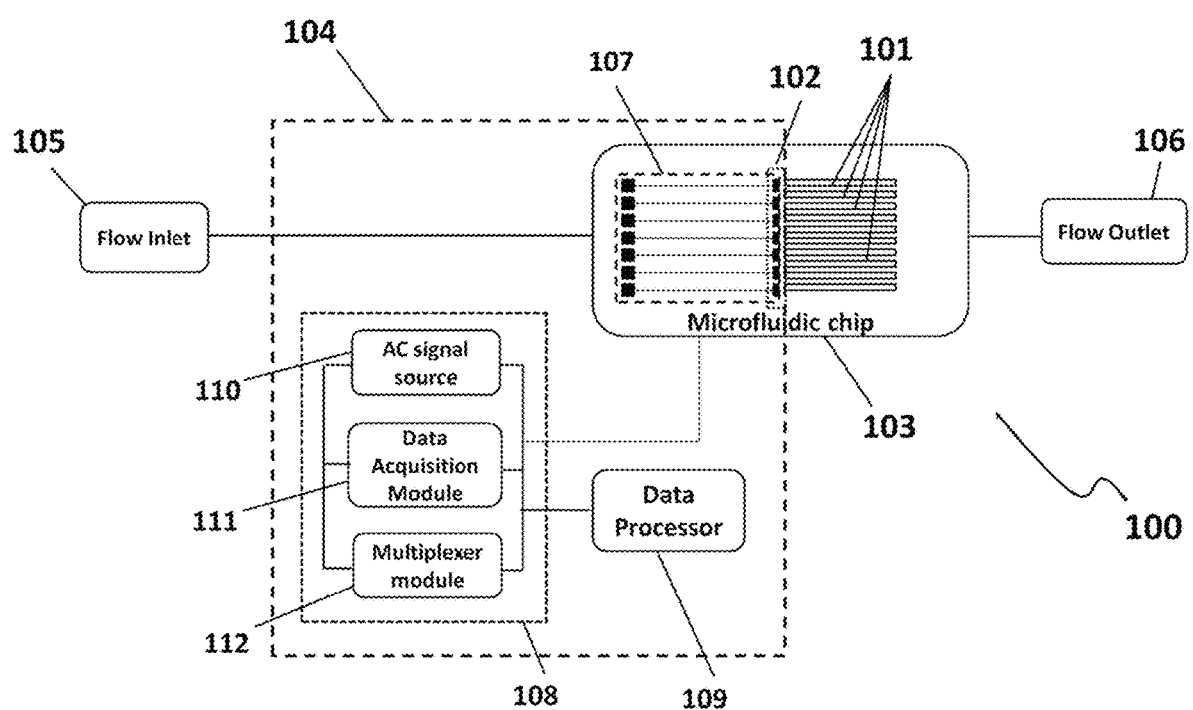
FIG. 1 illustrates an example system for isolating and diagnosing circulating tumor cells (CTCs) within a cellular sample.

The following detailed description is presented to enable a person skilled in the art to make and use the application. For purposes of explanation, specific nomenclature is set forth to provide a thorough understanding of the present application. However, it will be apparent to one skilled in the art that these specific details are not required to practice the application. Descriptions of specific applications are provided only as representative examples. Various modifications to the preferred implementations will be readily apparent to one skilled in the art, and the general principles defined herein may be applied to other implementations and applications without departing from the scope of the application. The present application is not intended to be limited to the implementations shown, but is to be accorded the widest possible scope consistent with the principles and features disclosed herein.

RBCs and WBCs have smaller average sizes compared to CTCs. Therefore, CTCs can be distinguished from RBCs and WBCs utilizing size-based CTC detecting systems. However, the size overlap between WBCs and CTCs would strongly decrease the efficiency of such systems. About 4% of WBCs, such as monocytes and eosinophil, have a size range of between about 12 µm to about 20 µm, which is comparable with the size of CTCs (i.e., 12 to 35 µm depending on the type of cancer). So, at least 40,000 WBCs with similar sizes to CTCs exist in each milliliter of a blood sample. Therefore, parameters of cells other than their size must be utilized to distinguish ECTCs and MCTCs from WBCs.

Disclosed herein is an integrated system and a method for isolation and detection of CTCs. The system can include a first mechanism for isolating CTCs along with other large biological cells from a blood sample and a second label-free mechanism for detecting the presence of CTCs among the isolated cells. In one implementation of the system of the present disclosure, the blood sample flows through a number of microchannels that are configured to only let smaller biological molecules to pass through. CTCs and large white blood cells (WBCs) in the blood sample are trapped at the inlet of the microchannels due to their larger size. Then, both types of CTCs, including epithelial circulating tumor cells (ECTCs) and mesenchymal circulating tumor cells (MCTCs), can be distinguished from WBCs based on their respectively different membrane capacitance or electrical impedance. In an aspect, membrane capacitance or electrical impedance can be directly measured by conductive silicon nano-grass (SiNG) electrodes. The SiNG electrodes can be patterned and etched, for example, at the inlet of the microchannels. The presence of SiNG can enhance the quality of signal extraction from the entrapped cells without inducing any damage or membrane rupture to the cells.

As used herein, the term "microchannel" refers to a channel having one inlet and one outlet for fluid flow with a micrometer sized depth and width that are configured for a size-based screening. The microchannels as used herein may have a depth of, for example, about 15 µm and a width of, for example, about 12 µm, so that large biological cells such as CTCs having a cell size larger than about 12 µm can be trapped or captured at the inlet of the microchannels.

As used herein, the terms "microfluidic chip" refers to a chip having at least an array of microchannels vertically etched on it that can be configured for size-based isolation or screening.

In one implementation, the disclosed system for isolating and diagnosing CTCs within a cellular sample may include two mechanisms for isolation and diagnosis of CTCs within a cellular sample, including: an isolating mechanism for isolating and trapping large biological cells based on size difference among the cells; and a diagnosing mechanism for diagnosing or detecting CTCs based on the electrical impedance difference among the trapped large biological cells. The cellular sample may include a blood sample, which may include red blood cells (RBCs), white blood cells (WBCs), and circulating tumor cells (CTCs). The large biological cells may have a size of greater than or equal to 12 µm, and may include CTCs and a number of large WBCs. The CTCs may include ECTCs, MCTCs, or both.

FIG. 1 illustrates a schematic of one example of a system 100 according to one or more aspects of the present disclosure, configured for isolating and diagnosing CTCs within a cellular sample. The system 100 can include: a mechanism for isolating and trapping large biological cells based on their size difference using an array of microchannels 101 for trapping large biological cells in a detection zone 102 at the entrance (i.e., inlet) of the microchannels 101. The microchannels 101 can be vertically etched on a microfluidic chip 103. The system 100 can include a mechanism for diagnosing or detecting circulating tumor cells (CTCs) based on the electrical impedance difference among the trapped biological cells via a diagnosing system 104. Both the mechanism for isolating large biological cells and the mechanism for diagnosing CTCs may be incorporated into the integrated individual system 100. Furthermore, the system 100 can include a flow inlet 105 configured for introducing an inlet flow that contains the cellular sample, for example, a blood sample into the microfluidic chip 103; and a flow outlet 106 configured for collecting an outlet flow that contains the remainder of the sample from the microfluidic chip 103. The flow inlet 105 may be configured to include a syringe pump. The flow outlet 106 may be configured to include a simple dish (i.e., collecting dish).

Referring to FIG. 1, the diagnosing system 104 can include: a plurality of electrical sensors 107 etched and positioned on a portion of the microfluidic chip 103, where the isolated and trapped large biological cells are attached to these electrical sensors; a signal controlling system 108 configured for applying an electrical signal to the trapped biological cells attached to the electrical sensors 107 and acquiring the corresponding electrical response as a criterion of the electrical impedance of the trapped and attached biological cells; and a data processor 109 configured for recording and analyzing the electrical response in order to detect the presence of the CTCs among the isolated large biological cells.

With further reference to FIG. 1, the signal controlling system 108 can include: an AC signal source 110 configured for applying the electrical signal to the electrical sensors 107; a data acquisition module 111 configured for acquiring the electrical response corresponding to the electrical signal from the electrical sensors 107, and a multiplexer module 112 configured for selecting and controlling the electrical sensors 107 for applying the electrical signal and acquiring the electrical response. The AC signal source 110 can be configured to apply a voltage of, for example, about 40 mV to the electrical sensors 107. Accordingly, the applied voltage may cause a frequency that ranges from about 100 Hz to about 100 KHz.

Figure 2A:
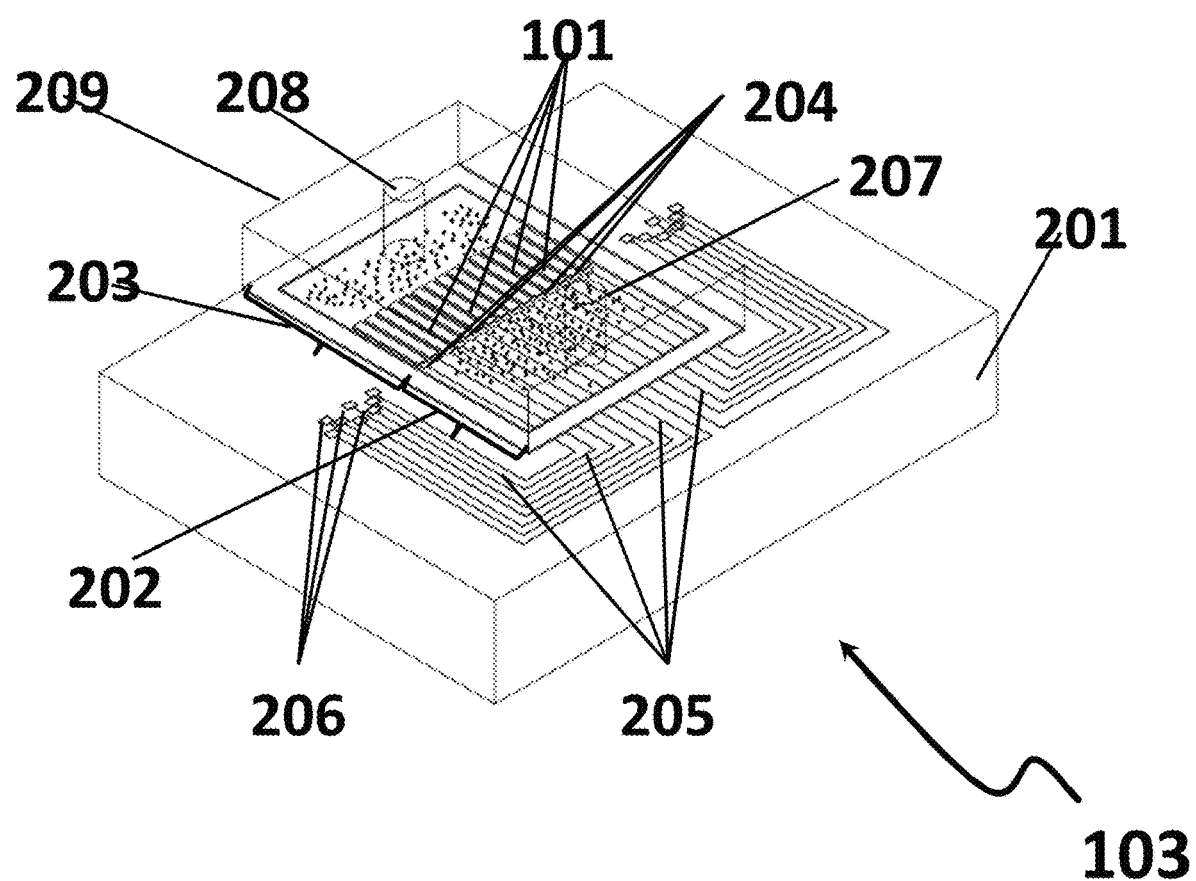
FIG. 2A is a schematic of one example of a microfluidic chip, according to one or more aspects of the present disclosure.
Figure 2B:
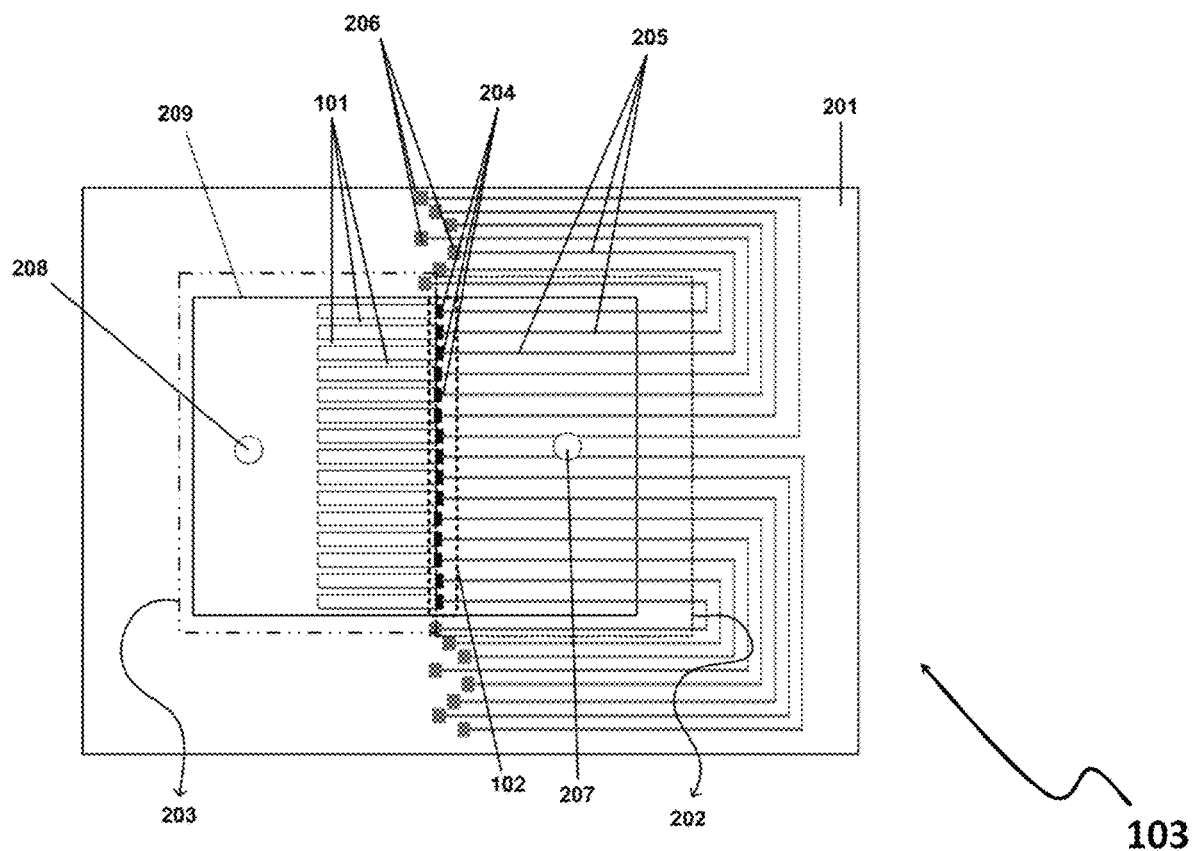
FIG. 2B is a schematic top view of one example of the microfluidic chip, according to one or more aspects of the present disclosure.

FIG. 2A is a schematic of one example of the microfluidic chip 103, and FIG. 2B is a top view of the same microfluidic chip 103. Referring to FIGS. 2A and 2B, the microfluidic chip 103 can include a chip 201 having an input part 202 and one output part 203 for fluid flow that is positioned onto the chip. An array of parallel microchannels 101 can be vertically etched onto the output part 203 of the microfluidic chip 103. The microchannels 101 can have a width of, for example, about 12 µm and a depth of, for example about 15 µm. In addition, an array of electrical sensors 107 can be embedded onto the chip 201, wherein each electrical sensor can include one electrode 204 placed within the input part 202. The electrode 204 can be connected to a readout pad 206 via an electrical conductive path 205 on the chip 201. Each electrode 204 can be positioned within the input part 202 at the entrance (i.e., inlet) of each microchannel 101. The electrodes 204 can include silicon nano-grass (SiNG) electrodes. The electrical sensors 107 can be patterned on the chip 201 via a photolithography method and be fabricated by a reactive ion etching (RIE) method at the inlet of the microchannels 101. The electrical conductive path 205 and the readout pads 206 can be made of gold. Furthermore, the microfluidic chip 103 can include an electrical insulating layer capped or bonded on top of the surface of the microfluidic chip 103 for electrical insulation. The insulating layer may be prepared and bonded via a plasma treatment. The insulating layer may include a polydimethylsiloxane (PDMS) layer.

Referring to FIGS. 2A and 2B, the microfluidic chip 103 (labeled in FIG. 1) can include a cylindrical inlet 207 that can be positioned vertically within the input part 202 of the chip 103. The cylindrical inlet 207 can be connected to the flow inlet 105 (labeled in FIG. 1) to introduce a flow including the cellular sample into the input part 202, an cylindrical outlet 208 that can be positioned vertically within the output part 203 of the chip 103 can be connected to the flow outlet 106 (labeled in FIG. 1) to discharge the remainder of the cellular sample, and a vertically positioned shield 209 surrounding the input 202 and output parts 203 of the chip.

In another aspect, a method for isolating and diagnosing of CTCs from a cellular sample is described. The cellular sample may be a blood sample including ECTCs, or MCTCs, or both. This method may be used, for example, for cancer diagnosis, investigating metastatic stage, or generally for cancerous state determination of a tumor metastasis.

In one implementation, the method for isolating and diagnosing of CTCs from a cellular sample can include steps of: isolating or screening the CTCs along with other large biological cells from a cellular sample based on the size difference among biological cells, and detecting the CTCs presence and concentration in the cellular sample based on electrical impedance difference of CTCs with other cells within the cellular sample. FIG. 1 system 100 can be utilized to implement the method for isolating and diagnosing of CTCs.

Referring to FIG. 1, in the first step of the method, a cellular sample is introduced into the microfluidic chip 103 via the flow inlet 105. The cellular sample flows from the inlet 105 to the outlet 106 of the microfluidic chip 103, so that the CTCs among other large biological cells are trapped at the inlet of the microchannels 101, herein named as detection zone 102. The trapped cells can then be attached to the SiNG electrodes of the electrical sensors 107. The introduced cellular sample may have a volume of, for example about 5 ml, and can flow with a flow rate of, for example about 20 µL/min to about 160 µL/min. During this step, the large sized cells including CTCs and large WBCs with a size range of about 12 µm to about 40 µm may be trapped at the inlet of microchannels.

Figure 3A:
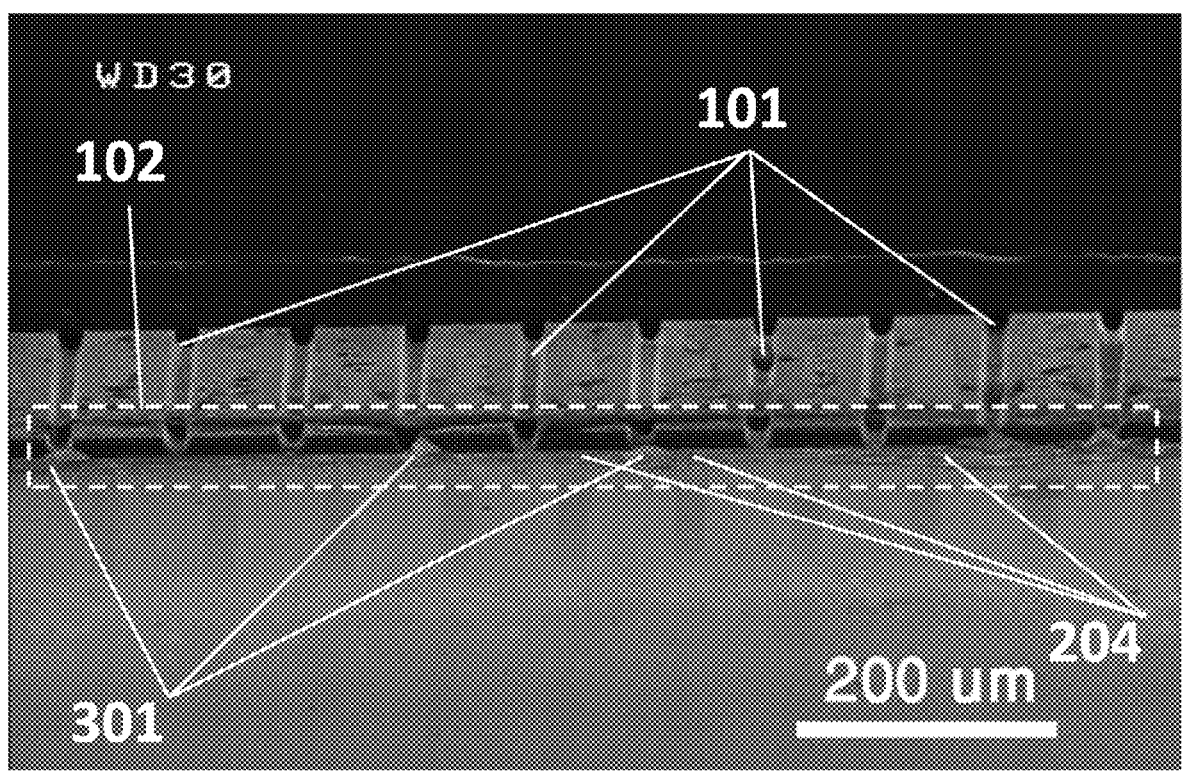
FIG. 3A illustrates a field emission scanning electron microscopy (FESEM) micrograph of an example entrapment of CTCs at the entrance of microchannel array.

FIG. 3A illustrates a field emission scanning electron microscopy (FESEM) micrograph of an example entrapment of CTCs 301 within the detection zone 102 at the entrance of microchannel array 101 on the SiNG electrodes 204.

Figure 3B:
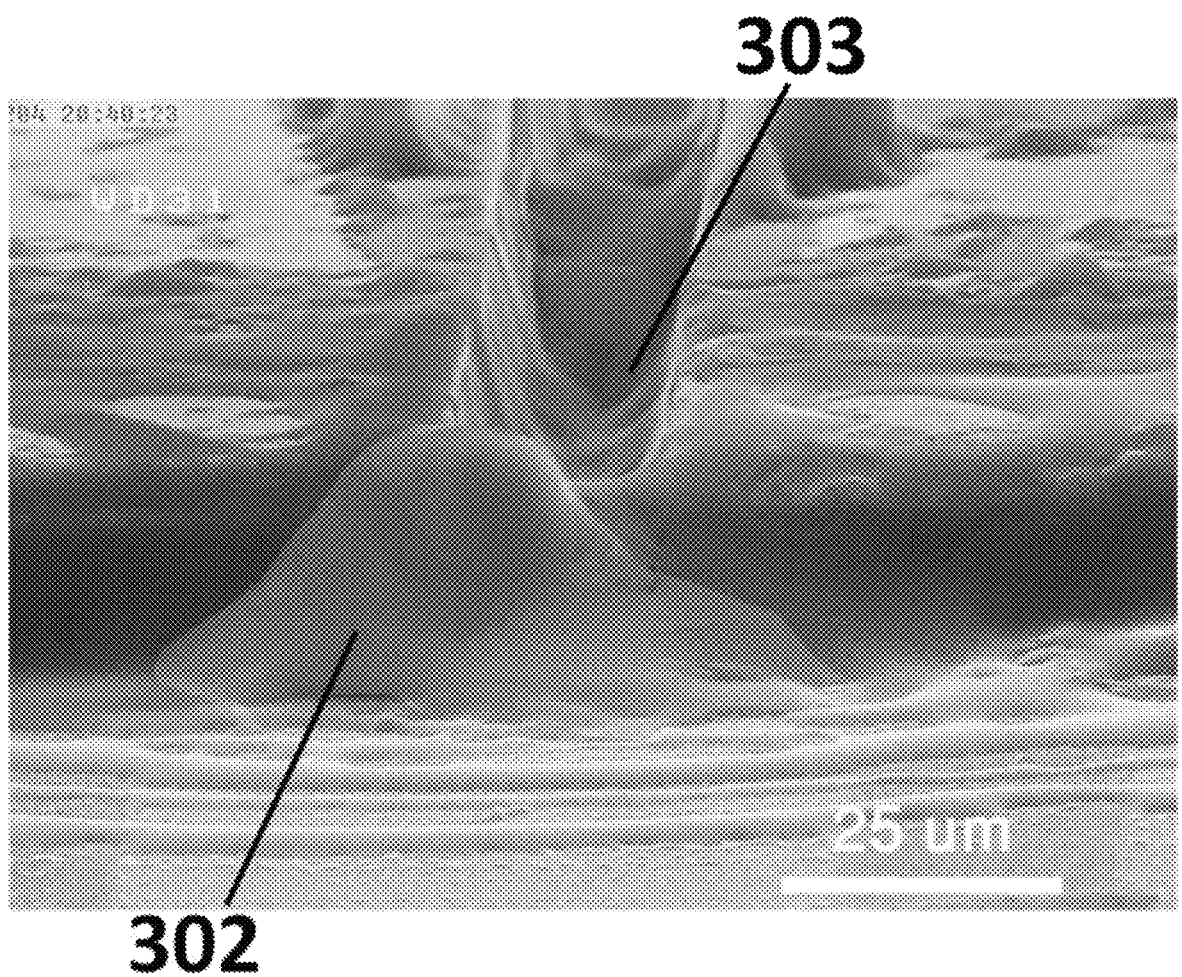
FIG. 3B illustrates a magnified field emission scanning electron microscopy (FESEM) micrograph of an example entrapment of a single CTC at the inlet of a microchannel.

FIG. 3B illustrates a magnified field emission scanning electron microscopy (FESEM) micrograph of an example entrapment of a single CTC 302 at the inlet of a single microchannel 303, according to systems and methods described herein.

Figure 3C:
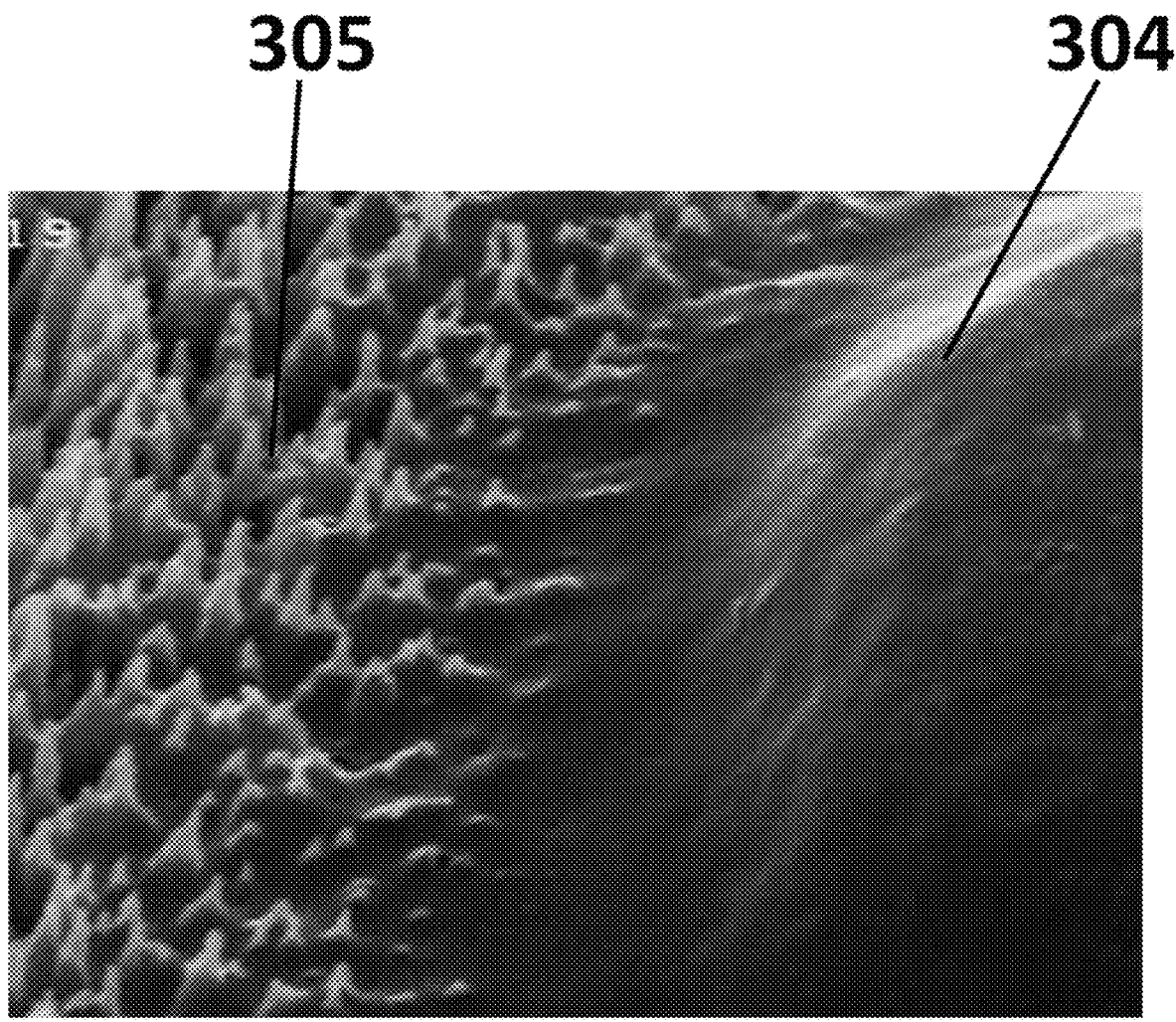
FIG. 3C illustrates a field emission scanning electron microscopy (FESEM) micrograph of an example direct interaction and attachment between SiNG electrodes and membrane of captured cells, as described in connection with one or more aspects of the present disclosure.

FIG. 3C illustrates a field emission scanning electron microscopy (FESEM) micrograph of an example direct interaction and attachment between the membrane of a captured cell 304 and the SiNG electrodes 305. As observable from this figure, nano-grass-incorporated silicon electrodes (SiNGs) 305 form a suitable sensing media as they provide many electrically active adhesive sites for the cell membrane.

Moving on to the second step of the method for isolating and diagnosing of CTCs from a cellular sample, the entrapped cells at the entrance of microchannels that are attached to the SiNG electrodes are electrically analyzed to detect CTCs using the diagnosing system 104 described above. The detecting of CTCs includes applying an electrical signal to the SiNG electrodes 204 using the signal controlling system 108, measuring the electrical response of the electrode using the signal controlling system 108, and recording and processing the electrical response from the electrodes via the data processor 109.

Electrical measurements may be performed before, during, and after flowing of the cellular sample through the microfluidic chip and an average value may be used to achieve an accurate analysis. Real-time monitoring of the channels may be performed by applying a bias voltage of 40 mV on each couple of electrodes and measuring the impedance at frequencies ranging from 100 Hz to 100 kHz to ensure the recording of any cellular capturing interactions with the SiNG electrodes.

EXAMPLES

Example 1: Investigating the Biocompatibility of SiNG Electrodes

In this example, in order to investigate the biocompatibility of silicon nano-grass electrode arrays during their direct interaction with captured cells, a MTT (3-(4, 5-dimethyl thiazol-2-yl)-2, 5-diphenyltetrazolium bromide) assay was used. First, some nano-grassed silicon wafers were prepared and sterilized by autoclave; then, the Huvec cells were seeded on Silicon nano-grass surface; after about 24 hours, the cells were detached from the substrate by trypsin and the cell culture media was added to the cell solution. Subsequently, the cells were placed in the wells of a sterile 96-well micro-plate with the same concentration and the MTT protocol was applied on each well.

This assay verified the viability of the cells based on colorimetric measurement. The reduction of yellow tetrazole to purple formazane is related to the ratio of remained live cells. Metabolic activity of the cells depends on the density deviations of this color in the Huvec cell solution. In this regard, about 10 µl of MTT solution (Sigma-Aldrich) with a concentration of about 5 mg/µl was added to each well. The wells were incubated for about 4 hours in a 5% $CO_2$ ambient at a temperature of about 37° C. Next, the float materials were removed from the surface of the wells and about 100 µl of dimethylsulfoxied (Sigma-Aldrich) was added to each well. After about 20 min stirring of each well (in order to solving the formazane), the optical absorption of cells contained in the wells was calculated in excitation wavelength of 493 nm by micro-plate reader system.

Figure 4:
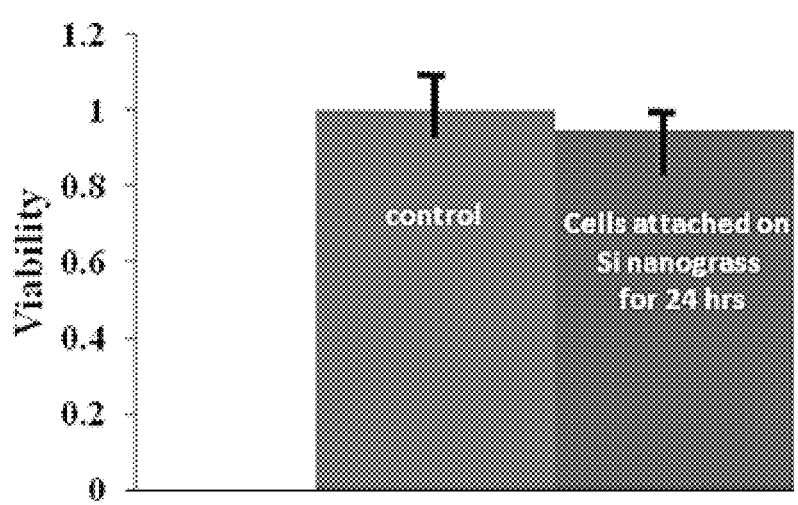
FIG. 4 illustrates 3-(4,5-Dimethylthiazol-2-yl)-2,5-Diphenyltetrazolium Bromide (MTT) assay results of a sample of Huvec cells seeded on Silicon Nano-grass (SiNG) surface.

FIG. 4 illustrates the MTT assay results diagram for cells attached on Silicon nano-grass surface after about 24 hours in comparison with the control sample. It is observable that the results for both indicate well acceptable biocompatibility of Silicon nano-grass with respect to CTRL sample (cell culture micro-wells).

Example 2: Isolating and Detection of ECTCs

In this example, MCF-7 cell line which is epithelial type of breast cancer (size: 15-35 µm), was obtained from the standard cell banks of national cell bank of Iran (NCBI). The cells were kept at a temperature of about 37° C. in a $CO_2$ incubator (5% $CO_2$, 95% air) in RPMI-1640 medium (Sigma 8758) which was supplemented with 5% fetal bovine (Gibco) serum and 1% streptomycin (Gibco). The fresh medium was replaced every day. Cells were stably stained by acridine orange (A/O) in their live state to enable capturing of fluorescent images of the trapped cells after every experiment. The cells were counted using an Auto Analyzer (Sysmex KX21) and distribution of leukocytes was as follows: 48.2% neutrophils, 4.2% eosinophils, no basophils, 43.1% lymphocytes, and 4.5% monocytes. Then, cells were suspended in about 50 ml of Dextrose-Sucrose (DS) to reduce the conductivity of the solution (DS dielectric constant: 80) and then they were added to about 0.5 ml of unprocessed blood as a carrier solution containing 6.1 k/µl white blood cells (WBCs). For calibration purposes and to ensure the precise measurements of the electrical data on the nature of the captured cells, the blood cells were stained using Cyto Red so that they could be easily distinguished from the CTCs during entrapment. The final solution was divided into 10 individual samples (with a volume of about 5 mL to prevent possible clogging).

Live florescent imaging was individually done on MCF-7 cells that were stained with A/O (green) and WBCs stained with Cyto Red (Red) as per the manufacturer's instructions and held in incubator for about 20 min. Then, the prepared cell samples containing MCF-7 cell line (ECTC) were introduced into syringe pump and delivered to the microfluidic chip with a flow rate of about 80 µL/min. Phase-contrast images of the cells were taken after their entrapment at the entrance of the microchannels using a JENUS fluorescent microscope with a CCD camera in the monochromatic phase-contrast mode.

Figure 5:
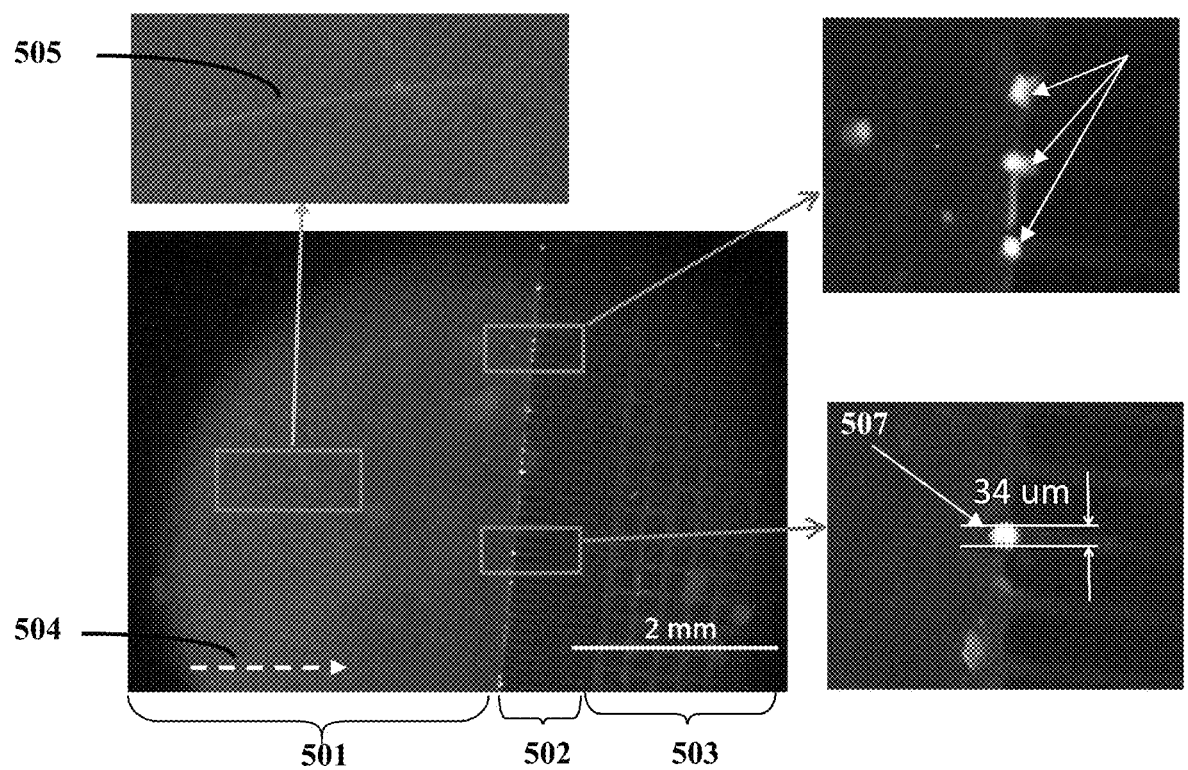
FIG. 5 illustrates fluorescence images of entrapped MCF-7 at the entrance of microchannels.

FIG. 5 illustrates fluorescent images of the ECTCs (MCF-7) that were taken after their entrapment at the entrance of microchannels. The FIG. 5 images show the input side 501 of the microfluidic chip, the microchannels 502 and the output side 503. Flow direction is indicated by a dashed arrow 504. The path 505 shows tracking of a single-cell movement toward channels 502. The trapped ECTCs (MCF-7) 506 and 507 at the entrance of the microchannels 502 are shown having a cell size about 34 µm for the single ECTC 507.

Electrical measurements were performed before, during, and after flowing of the cell sample solution through the chip. The real-time monitoring of the channels was performed by measuring the impedance, at frequencies ranging from about 10 kHz to about 50 kHz. The measurements were performed with an applied voltage of about 40 mV on each couple of SiNG electrodes. The signaling was repeated after the solution left the microfluidic chip to ensure any cellular capturing interaction with SiNG electrodes and the final electrical spike of each channel was the mean value of 10 subsequent measurements. To eliminate the effect of medium, the differentiated impedance value has been calculated by comparing the response of the electrodes in various stages of solution flow.

Figure 6:
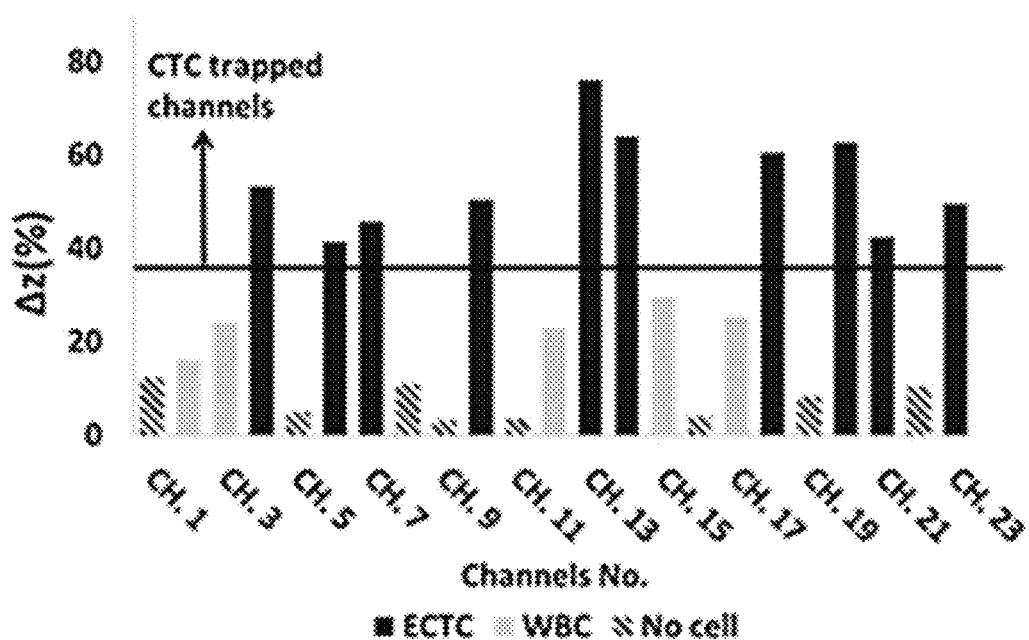
FIG. 6 illustrates epithelial circulating tumor cells (ECTCs) spiked after being captured by channels of an example microfluidic chip with single-cell resolution, representing the cell impedance changes versus channels numbers.

FIG. 6 illustrates the cell impedance changes versus channels numbers, representing ECTCs (MCF-7) spiked after being captured by the channels of the microfluidic chip with single-cell resolution. Different intensity of the electrical spikes measured by the SiNG electrodes can distinguish between entrapped CTCs and WBCs. The error bars represent the standard error of the mean (number of measurements on each channel=4). It can be seen from this figure that the impedance changes at the channels closed by different MCF-7 cells (ECTCs) show deviations from about 42% to about 75% (black columns). Thus, the impedance at the channels closed by entrapped ECTCs shows about 1.3 to about 5 times further variations than that of closed by trapped WBCs.

Figure 7:
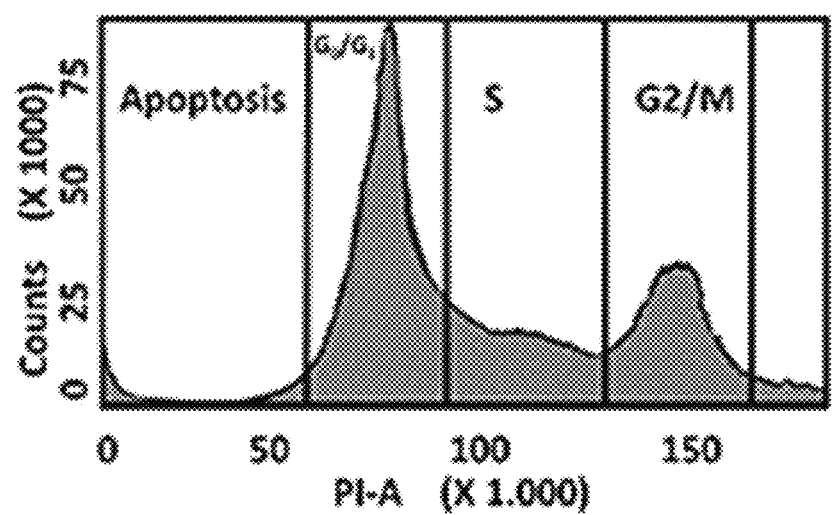
FIG. 7 illustrates flow cytometry analysis of MCF-7 cells showing distributed stages between the growth ($G_0$) and mitosis ($M_2$) stages.

Referring again to FIG. 6, comparing the responses of CH.15 vs. CH.6 and CH.2 vs. CH.13 indicates the minimum (45% vs. 25%) and maximum (77% vs. 16%) impedance variations between WBC and ECTC trapped channels. This might be related to the shape, size and state (from $G_0$ to $M_2$) of the cancer cells during entrapment. Referring to FIG. 7, the flow cytometry analysis taken from the CTC samples indicated that the cells were distributed between the $G_0$ and $M_2$ states. The coefficient of variation (CV) of the G0G1 peak of MCF-7 cells was 4.3 and the cell cycle phase fractions of G0G1, S and G2M were 47.9%, 21.9% and 30.2%, respectively. Hence, the various vital states and microtubule (MT) configurations of the CTCs might lead to their different electrical responses after entrapment. However, such distributed responses did not show any overlapping with entrapped blood cells.

Example 3: Isolating and Detection of MCTCs

In this example, MDA-MB231 cell line, which is a mesenchymal type of breast cancer was obtained from the standard cell banks of national cell bank of Iran (NCBI). Cells were kept at a temperature of about 37° C. in a $CO_2$ incubator (5% $CO_2$, 95% air) in RPMI-1640 medium supplemented with 5% fetal bovine serum and 1% streptomycin. The fresh medium was replaced every other day. Cells were stably stained by acridine orange (A/O) in their live state to enable the capture of fluorescent images of the trapped cells after every experiment. The cells were counted using an Auto Analyzer (Sysmex KX21) and suspended in about 50 ml of Dextrose-Sucrose (DS) added to 0.5 ml of unprocessed blood as a carrier solution containing 6.1 k/µl WBCs. The distribution of leukocytes was: 48.2% neutrophil, 4.2% Eosinophil, no basophil, 43.1% lymphocyte and 4.5% monocytes. For calibration purposes and to ensure precise measurements of the electrical data on the nature of the captured cells, the blood cells were stained using Cyto Red so that they could be easily distinguished from the CTCs during entrapment. The final solution was divided into 10 individual samples (with a volume of about 5 mL to prevent possible clogging of the microchannels). Live florescent imaging was individually done on MDA-MB231 cells that were stained with A/O (green) and WBCs stained with Cyto Red (Red) as per the manufacturer's instructions and kept in incubator for about 20 min. Then, the 10 cell samples prepared from MDA-MB231 cell line (MCTC) were introduced into the syringe pump and delivered to the microfluidic chip with a flow rate of about 80 µL/min. Phase-contrast images of the cells were taken after their entrapment at the entrance of the microchannels using a JENUS fluorescent microscope with a CCD camera in the monochromatic phase-contrast mode.

Figure 8:
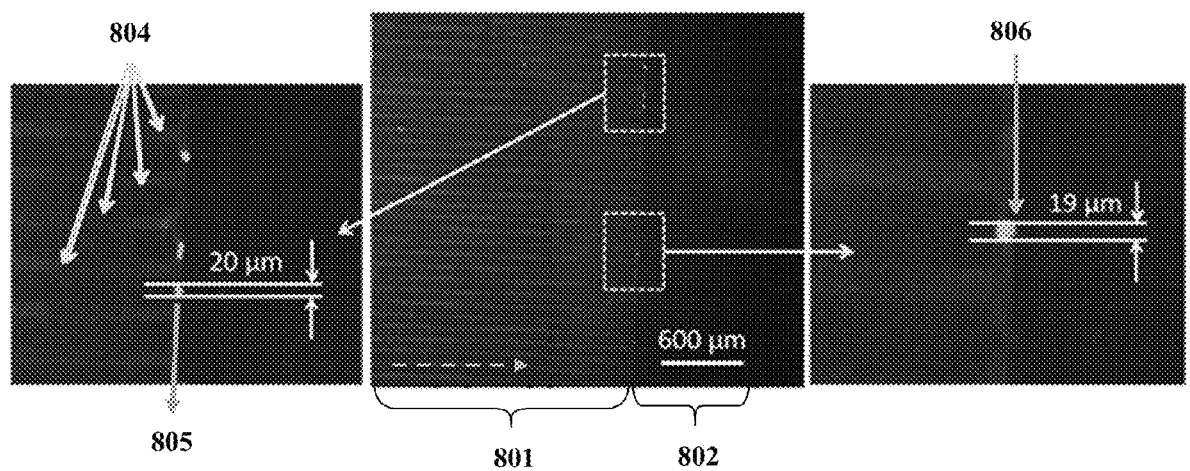
FIG. 8 illustrates phase contrast images of the MDA-MB231 after their entrapment at the entrance of microchannels.

FIG. 8 shows phase-contrast fluorescent images of the MCTCs (MDA-MB231), taken after their entrapment at the entrance of microchannels by JENUS florescent microscopy with a CCD camera using monochromatic phase contrast mode. The inlet side 801 of the microfluidic chip, the microchannels within the output side 802 and the flow direction 803 are shown in this figure. In addition, the magnified images of the central image show the SiNG electrodes and Au electrical path 804. Furthermore, two single MCTCs 805 and 806 have been magnified in this figure, presenting a cell size of about 20 µm (cell 805) and 19 µm (cell 805).

Electrical measurements were performed before, during, and after flowing of the solution through the chip. Real time monitoring of the channels was performed by measuring the impedance at the frequencies ranging from about 10 kHz to about 100 kHz and measurements were performed with an applied voltage of about 40 mV on each couple of SiNG electrodes. The signaling was repeated after the solution left the NELMEC chip to ensure any cellular capturing interaction with SiNG electrodes and the final electrical spike of each channel was the mean value of 10 subsequent measurements. To eliminate the effect of medium, the differentiated impedance value has been calculated by comparing the response of the electrodes in various stages of solution flow.

Figure 9:
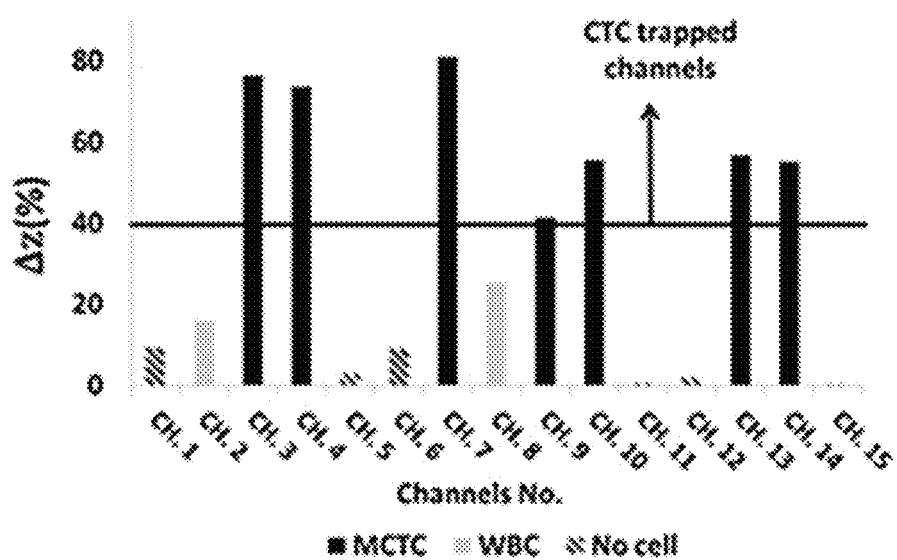
FIG. 9 illustrates impedance changes versus channel numbers, representing MDA-MB23 spiked after being captured by the channels of the microfluidic chip with single-cell resolution.

FIG. 9 illustrates the cell impedance changes versus channels numbers. The impedance changes in the channels enclosed by different MDA-MB231 cells (MCTCs) show deviations from about 42% to about 82% (black columns in FIG. 9) and the impedance changes of the microchannels entrapped the MCTCs were about 1.8 (Ch9 vs. Ch8) to 6 (Ch7 vs. Ch2) times further than that entrapped WBCs. As discussed in Example 2 hereinabove, this might be related to the shape, size and state (from $G_0$ to $M_2$) of the cancer cells during entrapment.

Figure 10:
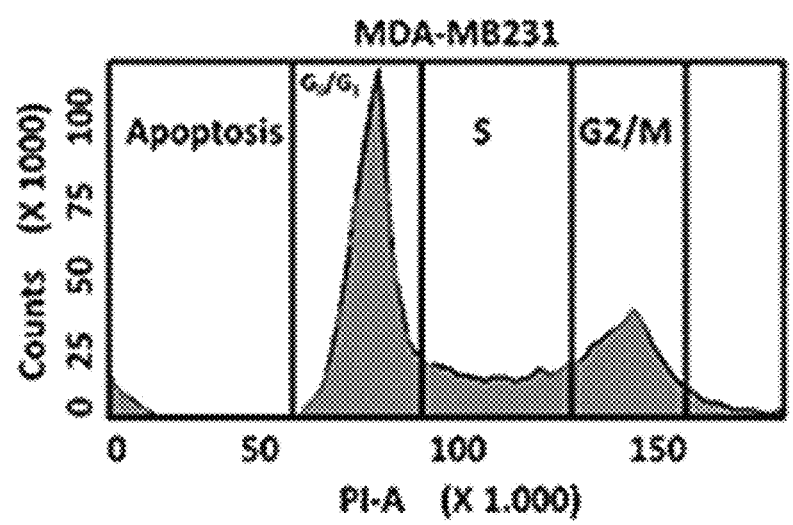
FIG. 10 illustrates a flow cytometry analysis taken from MDA-MB23 samples indicating that the cells were distributed between the growth ($G_0$) and mitosis ($M_2$) stages.

FIG. 10 shows the flow cytometry analysis taken from the MDA-MB231 cells indicated that the cells were distributed between the $G_0$ and $M_2$ states. The cell cycle phase fractions were 59.8% for G0G1, 15.5 for S and 33.7% for G2M.

Hence, the various vital states and also microtubule (MT) configurations of the MCTCs might lead to their different electrical responses after entrapment. However, such distributed responses did not show any overlapping with entrapped blood cells.

Example 4: Simultaneously ECTCs and MCTCs Screening and Detection

In this example, MCF7 and MDA-MB231 cell lines are epithelial and mesenchymal types of breast cancer were obtained from the standard cell banks of national cell bank of Iran (NCBI). Both types of cells were prepared and delivered to the microfluidic chip, and then electrical measurements were performed before, during, and after flowing of the solution through the chip, identical to the methods and details described in Examples 2 and 3, hereinabove.

Figure 11A:
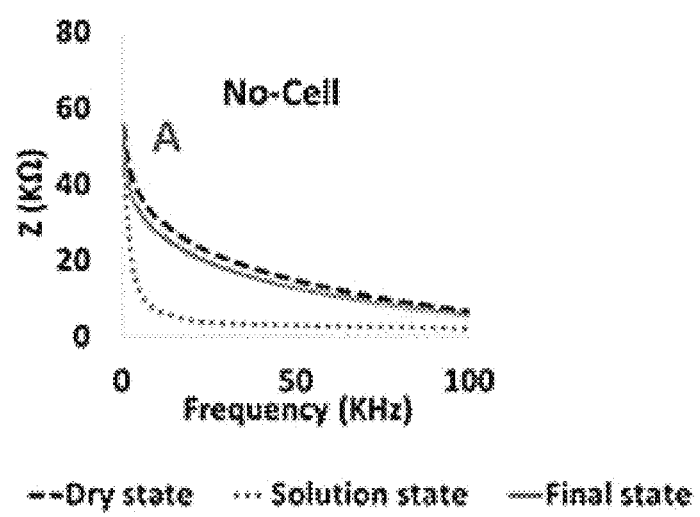
FIG. 11A illustrates a cell impedance versus frequency spectrum for an example open channel with no trapped cells at its entrance.
Figure 11B:
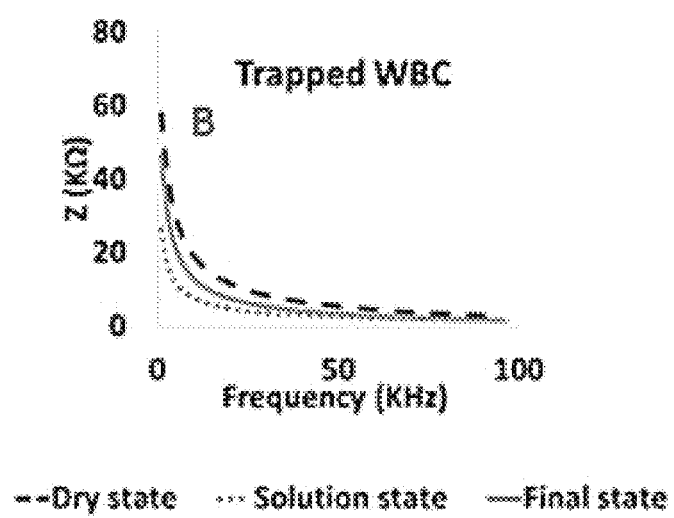
FIG. 11B illustrates a cell impedance versus frequency spectrum for an example closed channel with a white blood cell (WBC) trapped at its entrance.
Figure 11C:
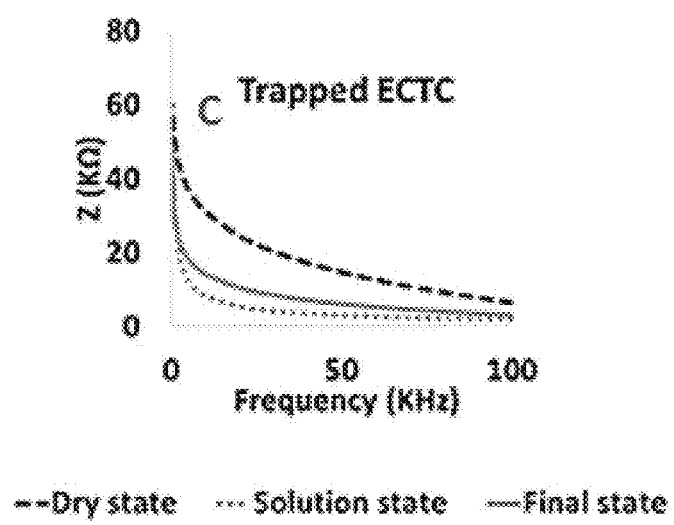
FIG. 11C illustrates a cell impedance versus frequency spectrum for an example closed channel with an epithelial circulating tumor cell (ECTC) trapped at its entrance.
Figure 11D:
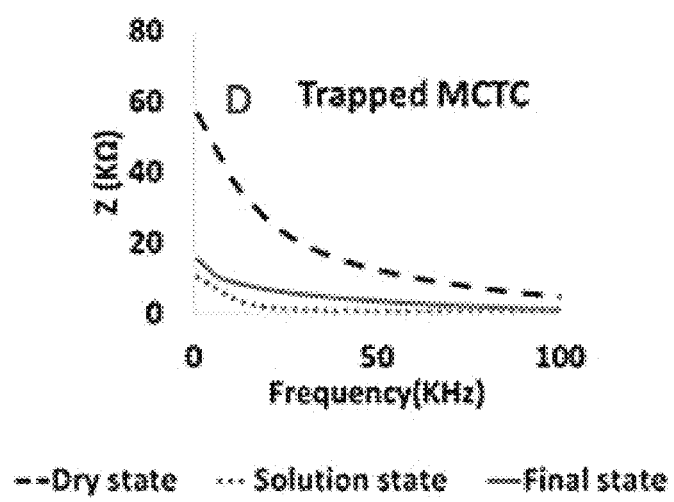
FIG. 11D illustrates a cell impedance versus frequency spectrum for an example closed channel with a mesenchymal circulating tumor cell (MCTC) trapped at its entrance.

Monitoring the time evolution of electrical responses of the electrodes during the flowing of sample blood cells can more effectively elaborate the detecting mechanism of microfluidic chip. FIGS. 11A, 11B, 11C and 11D represent the cell impedance versus frequency spectrum for 4 different channels including an open channel named as "No-cell" (FIG. 11A), a channel trapped by a WBC (FIG. 11B), a channel trapped by an ECTC (FIG. 11C) and a channel trapped by a MCTC (FIG. 11D). In these figures, the cell impedances were plotted for three time intervals, these being: i) before flowing the solution into the chip (dry state), ii) during the solution passing through the channels (solution state), and iii) after all of the solution left the microfluidic chip (final state). In dry state, the highest impedance value was measured for all of the channels. During the solution state, the impedances of both open and closed channels (by entrapped cell) are induced by carrier media solution. The entrapment of the cells at the opening of the channels during the solution state might be probable, but the presence of high resistive DS media could interfere the electrical response of the electrodes and suppress the significant spikes in enclosed channels. So, the solution state might not be best suited for detecting the nature of entrapped cells. In final state, the channels that remained open presented a high impedance similar to their initial dry state (solid curve in FIG. 11A). However, because of the cell membrane capacitance, the impedance of the channels closed by WBCs (FIG. 11B) or CTCs (FIGS. 11C and 11D) observably reduced with respect to their initial dry state and such reduction is much more significant in case of CTCs entrapped channels in comparison with WBCs entrapped channels. In addition, the measured impedance changes of the channels enclosed by MCTCs (FIG. 11D) was a little sharper than ECTCs (FIG. 11C).

Figure 12:
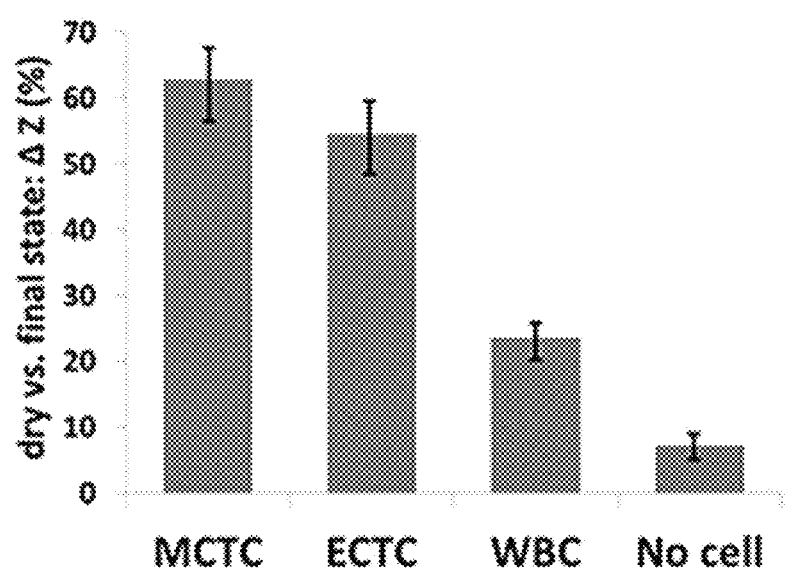
FIG. 12 illustrates mean impedance differences between dry state and final state of all open and closed channels versuseach type of trapped cells; the error bars represent the standard error of the mean (number of measured channels=15).

As a result, the impedance differences between the dry state and final state in each channel would be the indicative parameter for the nature of any entrapped cell. Referring to FIG. 12, the average of impedance differences between dry state and final state were plotted for all open and closed channels due to the nature of entrapped cells and it revealed that CTC entrapment induces considerable changes in the electrical response of the channels; so it's an electronic indication for CTC detection.

The aforementioned data completely support the increasing effect of EMT (epithelial-mesenchymal transition) on the membrane capacitance of tumor cells. The responses of the microfluidic chip to the blood sample reveal that this new architecture provides a reliable CTC detection assay by label-free electromechanical procedures.

What is claimed is:

1. An integrated system for isolating and diagnosing circulating tumor cells (CTCs) within a cellular sample, comprising:
    an isolating mechanism comprising an array of parallel microchannels vertically etched onto a microfluidic chip, each microchannel having a depth and a width, with one inlet and one outlet for fluid flow, the isolating mechanism configured to isolate and trap large biological cells at a detection zone from among the cellular sample flowing through the array of parallel microchannels based on cells size; and
    a diagnosing mechanism, configured to diagnose or detect CTCs among the trapped biological cells, based on cells electrical impedance, the diagnosing mechanism comprising:
        an array of electrical sensors, each electrical sensor comprising:
            one electrode being positioned within the detection zone onto the microfluidic chip within an input part at the inlet of each microchannel, each electrode comprising a plurality of silicon nano-grass (SiNG) arrays;
            a readout pad; and
            an electrical conductive path, wherein the electrode is connected to the readout pad via the electrical conductive path and the isolated and trapped large biological cells are attached to the electrodes;
        a signal controlling system connected to the array of electrical sensors, configured to apply an electrical signal to the trapped biological cells attached to the electrodes and to acquire an electrical response corresponding to the electrical signal from the trapped biological cells attached to the electrodes, the signal controlling system comprising:
            an AC signal source configured to apply the electrical signal to the electrical sensors;
            a data acquisition module configured to measure the electrical response from at least one couple of electrodes of the electrical sensors corresponding to the applied electrical signal, the electrical response comprising an electrical impedance measured at a frequency range between 100 Hz and 100 kHz; and
            a multiplexer module configured to select and control the electrical sensors for applying the electrical signal or acquiring the electrical response; and
        a data processor connected to the signal controlling system, the data processor configured to:
            analyze the electrical response by real-time monitoring the electrical response measured before, during, and after flowing of the cellular sample into the microfluidic chip; and
            detect CTCs among the isolated and trapped large biological cells responsive to a variation of the monitored electrical response being more than a threshold value.

2. The system according to claim 1, wherein CTCs comprise at least one of epithelial circulating tumor cells (ECTCs), mesenchymal circulating tumor cells (MCTCs), and combinations thereof.

3. The system according to claim 1, wherein the cellular sample comprises a blood sample.

4. The system according to claim 3, wherein the large biological cells comprise at least one of white blood cells (WBCs), CTCs, and combinations thereof.

5. The system according to claim 1, wherein the large biological cells have a size in a range of about 12 μm to about 40 μm.

6. The system according to claim 1, further comprising:
a flow inlet to introduce an inlet flow including the cellular sample; and
a flow outlet to collect an outlet flow including the cellular sample remaining after isolating.

7. The system according to claim 6, wherein:
the flow inlet comprises a syringe pump, and
the flow outlet comprises a collector dish.

8. The system according to claim 6, wherein the system further comprises:
an input part and an output part positioned onto the microfluidic chip for fluid flow;
an inlet with a cylindrical shape positioned vertically within the input part of the microfluidic chip, the inlet connected to the flow inlet; and
an outlet with a cylindrical shape positioned vertically within the output part of the microfluidic chip, the outlet connected to the flow outlet.

9. The system according to claim 6, wherein the isolating mechanism is configured to introduce the cellular sample into the microfluidic chip with a flow rate in a range between 20 μL/min and 160 μL/min to traverse the cellular sample from the inlet to the outlet,
wherein the CTCs are trapped at the inlet of the microchannels and attached to electrodes of the array of electrical sensors responsive to large size of CTCs.

10. The system according to claim 1, wherein:
the width of the microchannels is about 12 μm, and
the depth of the microchannels is about 15 μm.

11. The system according to claim 1, wherein the microfluidic chip comprises a silicon chip or wafer.

12. The system according to claim 1, wherein the detection zone comprises a zone at the inlet of the microchannels.

13. The system according to claim 1, wherein the diagnosing mechanism is configured to:
select at least one couple of electrodes of the array of electrical sensors using the multiplexer module;
apply an electrical signal comprising a voltage of about 40 mV to the at least one couple of electrodes using the AC signal source, the applied voltage has a frequency range between 100 Hz and 100 kHz;
measure a dry state electrical impedance of the at least one couple of electrodes at frequencies ranging from 100 Hz to 100 kHz using the data acquisition module before flowing the cellular sample into the microfluidic chip;
measure a final state electrical impedance of the at least one couple of electrodes at frequencies ranging from 100 Hz to 100 kHz using the data acquisition module after the cellular sample left the microfluidic chip;
record and process the electrical impedance from the electrodes using the data processor by calculating an electrical impedance difference between the dry state electrical impedance and the final state electrical impedance; and
detect via the data processor CTCs among the trapped biological cells at the detection zone responsive to the electrical impedance difference being more than the threshold value.

14. The system according to claim 1, wherein the threshold value comprises an increase of at least 40 percent in the monitored electrical response.

15. The system according to claim 1, wherein the readout pads comprise gold.

16. The system according to claim 1, wherein the electrical conductive path comprises gold.

17. An integrated system for isolating and diagnosing circulating tumor cells (CTCs) within a blood sample, comprising:
an isolating mechanism, configured to isolate and trap large biological cells at a detection zone from among the cellular sample based on cells size, the isolating mechanism comprising an array of parallel microchannels vertically etched onto a microfluidic chip, each microchannel having a depth and a width, with one inlet and one outlet for fluid flow, the detection zone comprising a zone at the inlet of the microchannels,
wherein the large biological cells comprise at least one of white blood cells (WBCs), CTCs, and combinations thereof; and
a diagnosing mechanism, configured to distinguish CTCs from WBCs, the diagnosing mechanism comprising:
an array of electrical sensors, each electrical sensor including one silicon nano-grass (SiNG) electrode connected to a readout pad via an electrical conductive path, and each electrode being positioned within the detection zone onto the microfluidic chip, wherein the isolated and trapped large biological cells are attached to the SiNG electrodes;
a signal controlling system electrically connected to the array of electrical sensors, comprising:
a multiplexer module configured to select and control at least one couple of SiNG electrodes of the array of the electrical sensors for applying an electrical voltage and measuring a respective electrical impedance;
an AC signal source configured to apply an electrical voltage of 40 mV with a frequency between 100 Hz and 100 kHz to the at least one couple of SiNG electrodes; and
a data acquisition module configured to:
measure a dry state electrical impedance of the at least one couple of electrodes corresponding to the applied voltage before flowing the cellular sample into the microfluidic chip; and
measure a final state electrical impedance of the at least one couple of electrodes corresponding to the applied voltage after the cellular sample left the microfluidic chip; and
a data processor electrically connected to the signal controlling system, the data processor configured to:
compare the dry state electrical impedance with the final state electrical impedance; and
detect CTCs trapped at the inlet of a microchannel between the at least one couple of electrodes responsive to a difference between the dry state electrical impedance with the final state electrical impedance being more than a threshold value.

18. The system according to claim 17, wherein the threshold value comprises at least 40 percent increase of the final state electrical impedance with respect to the dry state electrical impedance.

* * * * *